United States Patent [19]

Pfeiffer et al.

[11] Patent Number: 5,100,776
[45] Date of Patent: Mar. 31, 1992

[54] IMMUNOLOGICAL DETECTION PROCESS FOR HERBICIDES

[75] Inventors: Wolfgang Pfeiffer, Feldafing; Rudolf H. Dittel, Utting; Wolfgang Mies, Gauting, all of Fed. Rep. of Germany

[73] Assignee: Dr. Pfeiffer Bioanalytik KG, Inning, Fed. Rep. of Germany

[21] Appl. No.: 219,656

[22] Filed: Jul. 15, 1988

[30] Foreign Application Priority Data

Jul. 17, 1987 [DE] Fed. Rep. of Germany ....... 3723726

[51] Int. Cl.$^5$ .................... C12Q 1/00; G01N 33/53; G01N 33/543; G01N 33/537
[52] U.S. Cl. .................... 435/7.9; 435/961; 435/968; 436/518; 436/538; 436/542; 436/548; 436/805; 436/815; 436/822
[58] Field of Search .................... 435/7, 4, 18, 7.9; 436/532, 815

[56] References Cited

U.S. PATENT DOCUMENTS 4,530,786 7/1985 Dunbar et al. .................... 435/7

OTHER PUBLICATIONS

I. Dore et al., Immunochemical Studies of Tobacco Mosaic Virus-VII, Molecular Immunology, vol. 24, No. 12, pp. 1351-1358, May 1987.

Primary Examiner—Esther L. Kepplinger
Assistant Examiner—Jacintha M. Stall
Attorney, Agent, or Firm—Pravel, Gambrell, Hewitt, Kimball & Krieger

[57] ABSTRACT

The invention concerns an immunological detection process, with which triazines and structurally similar compounds and/or biologically equivalent compounds with similar bonding behavior are detected as belonging to one activity class, but with which on the other hand it is possible to identify the individual substances even in complicated mixtures.

12 Claims, No Drawings

IMMUNOLOGICAL DETECTION PROCESS FOR HERBICIDES

FIELD OF THE INVENTION

The invention concerns an immunological process for the detection of environmentally relevant substances, especially of pesticides, in the ground water or in drinking water.

BACKGROUND OF THE INVENTION

Recently alarming reports have been published, from which an impurification of the ground water, from which frequently drinking water is obtained without great expenditure for purification, by nitrates from fertilizers, by chlorinated solvents from dry cleaning operations, by herbicides (pesticides), insecticides and their decomposition products, emerges. In this process, the pesticide atrazine and its metabolites constitute the greatest problematical substance in drinking water.

Atrazine is a non-odiferous white powder having the chemical name 2-chloro-4-ethylamino-6-isopropylamino-1,3,5-triazine and it has been used for approximately thirty years all over the world as a herbicide. It prevents a photosynthesis and thereby causes "weeds" rapidly to wither. Atrazine is used in particular as a weed killer in corn fields, and 90% of all the corn fields in the Federal Republic of Germany are treated with atrazine, so that atrazine heads the list of substances used, with approximately 1000 tonnes per annum. Apart from atrazine, other triazine herbicides are employed, the presence of which in the ground and surface waters has been proven. Table 1 provides a survey of the most important triazine herbicides.

TABLE 1

Triazine-Herbicides

| Ametryn: | $R^1 = S-CH_3$, $R^2 = NH-CH(CH_3)_2$, $R^3 = NH-C_2H_5$ |
|---|---|
| Atraton: | $R^1 = O-CH_3$, $R^2 = NH-CH(CH_3)_2$, $R^3 = NH-C_2H_5$ |
| Atrazin: | $R^1 = Cl, R^2 = NH-C_2H_5$, $R^3 = NH-CH(CH_3)_2$ |
| Aziprotryn: | $R^1 = S-CH_3, R^2 = NH-CH(CH_3)_2$, $R^3 = N_1$ |
| Desmetryn: | $R^1 = S-CH_3, R^2 = NH-CH(CH_3)_2$, $R^3 = NH-CH_3$ |
| Dipropetryn: | $R^1 = S-C_2H_5$, $R^2 = R^3 = NH-CH(CH_3)_2$ |
| Methoprotryn: | $R^1 = S-CH_3, R^2 = NH-CH(CH_3)_2$, $R^3 = NH-C_3H_6-OCH_3$ |
| Prometryn: | $R^1 = S-CH_3, R^2 = R^3 = NH-C_3H_7$ |
| Propazin: | $R^1 = Cl, R^2 = R^3 = NH-C_3H_7$ |
| Simazin: | $R^1 = Cl, R^2 = R^3 = NH-C_2H_5$ |
| Terbumeton: | $R^1 = O-CH_3, R^2, R^3$ wie Terbutryn |
| Terbuthylazin: | $R^1 = Cl, R^2, R^5$ wie Terbutryn |
| Terbutryn: | $R^1 = S-CH_3, R^2 = NH-C(CH_3)_3$, $R^3 = NH-C_2H_5$ |

For a long time, it was assumed that these triazine compounds are permanently decomposed after use and are bound with particles of soil, so that danger to the ground water is excluded. But it has been found that the compounds are very stable, and that the time taken for half of the active ingredient to be decomposed in the soil amounts to between two and five months. In sandy soil as well as in soils which have little loam and clay, the active ingredient is relatively easily washed out into the ground water, in which the decomposition takes still longer, so that residues of triazines may appear years later in the ground water.

The drinking water regulations and the "European Community Guidelines on the Quality of Water for Human Consumption" lay down limit values for the amounts which are still tolerable of these substances in drinking water. For individual substances the maximal limit amounts to 0.0001 mg/l (100 ng/l), as a whole, the sum of these substances may not exceed the concentration of 0.0005 mg/l (500 ng/l). For a precise analysis, the detection limit should be one or two orders of magnitude below this value. However, the great number of substances in question and the low limit values raise a great problem for chemical analysis. Physical-chemical methods of analysis (GC,GC-MS, HPLC) require large-scale enrichment processes for identification and for quantification of chemical substances and they are very costly and time-consuming. In addition they do not allow any statement concerning the toxicity of the compounds. Modern biochemical analytical processes are represented by immunological test processes, the so-called "immuno-assays", in which cell components are used as the test substances. Immunological analytical processes constitute highly-sensitive rapid tests in the sector of waters analysis, and they guarantee frequently fast, economical and effective environmental monitoring.

Immuno-assays are highly sensitive test systems for the quantitative detection of substances on the basis of the antigen-antibody reaction. The antibodies are firstly induced by the immunization of laboratory animals and are extracted from their sera or from lymphocytes producing antibodies, and are purified via affinity columns, which contain as the filler material agarose, for example. Antibodies represent one of the natural defensive systems of higher animal life. The defensive function is based on the fact that specific antibodies are induced on the basis of natural infection or of artificial infection by vaccination. A definite size of molecule is a prerequisite for the formation of antibodies. If a specific antibody formation is to be initiated against very small molecules, for example plant protection agents, these (haptenes) must be coupled before immunization with a high-molecular carrier molecule, such as e.g. a protein (haemocyanine, beef serum albumin, ovalbumin, thyroglobulin, polylysin et al.).

For the detection of chemical substances, the antigen-antibody bonding is employed, which takes place when adding a sample which contains the chemical substance as antigen to the antibody. In the classical immunoassay the antigens to be detected compete with radioactively marked antigens of the same specificity around the bonding positions on the antibody. More recently enzyme immunoassay (EIA) has increased in significance in comparison to radio immunoassay (RIA). In this process the radioactive antigen is replaced by an enzyme-antigen conjugate, which can then compete with the sample antigen for the free bonding positions of the antibody. In this competing EIA, a predetermined quantity of the enzyme marked antigen competes with the sample antigens for the bonding positions on antibodies, which for their part are bonded adsorptively or covalently to a substrate, for example a polystyrene surface. With a small concentration of sample antigens many enzyme tracers are bonded (high substrate conversion), while with a high concentration of sample antigens, on the other hand, only a few enzyme tracers are bonded (low substrate conversion). Therefore the amount of the bonded enzyme tracer is a function of the sample antigen concentration. After the separation of the non-bonded enzyme tracer parts by means of a washing step, it is possible to detect the share of the bonded enzyme marked antigen on the basis of the conversion of the substrate, and therefore to detect the antigen concentration in the sample. The measurement magnitude for the bonding of the enzyme tracer is the absorption of the converted quantity of substrate.

Using the technology described above, specific antibodies are induced against various pesticides and are developed in immuno-assays with the aim of rapid, highly-specific and therefore economical detection of this problematic substance. However, it is often the case that with such an immuno-assay clear identification and quantification is not possible because of cross-reactions. By a cross-reaction what is means is the phenomenon that antibodies recognize common functionalities in molecules of different structures and classify these molecules in one activity class but are unable to differentiate between the individual molecules. This effect is found very clearly in the case of small molecules (antigens), because these must be bonded on a carrier matrix (protein) and therefore only the side facing away from the carrier matrix, but not the entire molecule, acts as the recognition region. Molecules with similar structure to the side which is turned away can then often not be distinguished in immunoassays. In many cases, on the other hand, the effect of the cross-reaction is even desirable, vice-versa, because not only the antigen used specially for the production of an antibody, but also compounds having a similar chemical structure or with similar biological activity to that of the antigen used can be detected. By a test with the deliberate use of cross-reactions, different substances which belong to the same activity class can be detected. This is very valuable in the toxicity evaluation of previously unresearched compounds. Animal tests and bioassays can therefore be reduced to the minimum necessary, because the potential danger of ecotoxicologically previously unresearched compounds is already recognizable in the foreground due to the activity class classification mentioned above.

SUMMARY OF THE INVENTION

The invention is based on the object of making available an immunological detection process, by means of which triazine herbicides and compounds with a chemically similar structure or with biologically similar activity can be properly detected as belonging to one activity class, but on the other hand it is possible as well to identify the individual chemical substances even in complicated mixtures unambiguously.

DETAILED DESCRIPTION OF THE INVENTION

The object above is attained by an immunological process for the detection of compounds having the following formula:

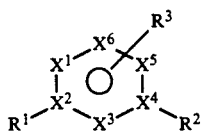
(I)

where:
$X^1$, $X^2$, $X^5$ are carbon or nitrogen;
$X^2$, $X^4$, $X^6$ are carbon;
$R^1$ is the group HN ($C_nH_{2n+1}$) wherein n is the integer from 0 to 8;
N ($C_mH_{2m+1}$)$_2$, where m is the integer 1 to 8;
HN-$C_nH_{2n}$Y, where Y is a cyano-, amino- or a COOH group and n is the integer 1 to 8;
$C_xH_{2x}$Z, where Z is a cyano-, amino- or COOH group, and x is the integer 1 to 8;
azide, halogen, an SH group, an OH group or a HN-$C_6H_4$Cl group;
$R^2$ is a group HN$C_qH_{2q+1}$, where q is an integer from 0 to 8;
N($C_rH_{2r+1}$) where r is the integer 1 to 8;
HN-$C_qH_{2q}$Y where Y is a cyano-, amino-, azido- or a COOH group and q is the integer 1 to 8;
N ($C_rH_{2r+1}$)Z, where Z is a cyano-, amino-, azido-, or COOH group or is a $C_qH_{2q}$ group,
and r is an integer from 1 to 8 and q is an integer from 1 to 8;
azide, halogen, an SH group or an OH group;
$R^3$ is halogen; $SC_nH_{2n+1}$ where n is an integer from 0 to 8; $OC_nH_{2n+1}$ where n is an integer from 0 to 8; a cyano-, amino-, carboxyl-, or a CHO group, where the substituent $R^3$ is either in the meta position to $R^1$ and $R^2$ or may be in ortho- or para-position to $R^1$ and $R^2$.

characterized in that by coupling a compound named above (I) (antigen) via the substituents $R^1$ or $R^2$ or $R^3$ with a matrix, respectively only a portion of the molecule of the compound (I) is exposed, and subsequently by the immunization of laboratory animals an antibody which preferably responds to this exposed portion of the molecule of compound (I) A, B or C is extracted, and for the immunological detection of the compound (I) a sample, which presumably contains it, is reacted with at least two of the above-named antibodies A, B or C in test series simultaneously or with different sequence of the named antibodies, and on the basis of the antigen-antibody bonding which is present for the respective test series, qualitative and quantitative determination is effected with respect to the compound (I).

In a preferred embodiment of the process in accordance with the invention, the compound of formula (I) constitutes a meta-substituted six-membered ring which is aromatic and which contains up to three nitrogen atoms. Particularly advantageous for this purpose are pyridine, pyrimidine or triazine.

A preferred application of the process in accordance with the invention is that for the immunological detection three anti-bodies A, B and C are used in test series in the following sequence:
1st test series: A B C
2nd test series: B C A
3rd test series: C A B.

The sample having the substance to be detected is advantageously reacted respectively and separately with each of the antibodies in use. This can be done in such a way that the solutions to be investigated are pipetted into the reaction vessels which are coated with the corresponding antibodies, or into the cavities of a microtiter plate thus coated.

Another preferred alternative is that the sample to be examined is initially reacted with the first antibody of the respective test series, then the non-reacted supernatent is separated and the latter is reacted respectively with the next antibody of the test series.

In special cases, it can be shown to be favourable when using the process according to the invention, to extract monoclonal antibodies during the preparation of the sera which are obtained from laboratory animals or lymphocytes producing antibodies by the hybridom technology and then to use them as antibodies in the detection process.

The immunological test process of the present invention makes it possible to detect, apart from the compound (I), by cross-reactivity structurally similar compounds as well which belong to this class of compounds and also other structurally different compounds, which however have the same biological activity and show similar bonding behavior. The immunological detection of the antigen/antibody reaction is effected advantageously in the process in accordance with the invention by using a corresponding antigen, which is radioactively marked, or which is bonded on an enzyme, on a fluorescent substance or on a substance which emits an electrical signal (biosensor). Sample antigens and marked or bonded antigens (detection agent) are caused to compete for the bonding positions of the antibody, then the free detection agent which is not bonded on the antibody is washed out and finally by the measurement of the radioactive radiation, of absorption, of fluorescence radiation or of the electrical signal, the amount of bonded detection agent and therefore the concentration of the antigen in the solution can be detected.

The present immunological detection method in accordance with the invention makes it possible to detect substances of a predetermined class of activity, and simultaneously to identify the different substances of this activity class.

A test process has been made available which operates rapidly, highly specifically and at low costs and which can deal with the high sampling loads in environmental analysis, which in spite of automation is not possible when using the conventional analytical methods. The process has been designed in such a manner that compounds which have previously not been researched as to their toxicity can be evaluated ecologically by the classification in activity classes.

The present invention will be explained in more detail below on the basis of the following examples.

EXAMPLE 1

Below the preparation of three different antibodies A, B and C, which are respectively and preferably directed against one side of the herbicide atrazine, a preferred compound from the series of compounds having the formula (I), and a method for the implementation of the immunological test process in accordance with the invention are described.

For the preparation of an antibody A, which is preferably directed against the side

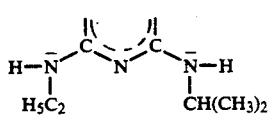

(II)

of the atrazine molecule, at first the methylthioether group of the triazine ametryn is sulfoxidized with peroxy acid and then the modified ametryn is coupled directly with the beef serum albumin. In the analogous way, for the development of an antibody B, which is preferentially directed against the side:

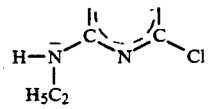

(III)

of the atrazine molecule, one of the ethylamino groups of the triazine simazine is bonded by the carbodiimide process to the protein. Lastly an antibody C which preferably responds to the side:

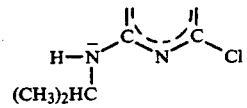

(IV)

of the atrazine is produced by coupling the herbicide propazine via one of the isopropylamino groups with the carrier matrix.

The conjugates prepared as above are inoculated for the generation of antibodies A, B and C in laboratory animals (rabbits) which are then extracted from the sera of the immunized animals by known processes or by affinity chromatography by substituents according to formula (I).

The antibodies obtained are adsorbed on the polystyrene surface of the microtiter cavities. To this end, the antibodies are dissolved in carbonate buffer ($Na_2CO_3$/$NaHCO_3$: 50 mmol/liter; pH 9.6) and respectively 0.25 ml of the solution obtained is pipetted into the individual cavities of the microtiter plate. In the following incubation takes place overnight at room temperature and washing takes place next day with TBS buffer. The well covered plates are then stored dry at $-20°$ C. For analysis 180 $\mu l$ of the aqueous sample to be investigated (concentration of the substance investigated is from 1 $\mu g/l$ to 200 mg/l) are poured into the cavities and respectively 50 $\mu l$ enzyme tracer, a conjugate of alkaline phosphatase and a triazine, which is selected depending on the type of the antibody, are added in the cavities. If the detection is carried out with antibody A, ametryn is coupled with the enzyme, but if antibody B or antibody C are present, simazine or propazine are used.

The solutions are mixed by brief horizontal shaking of the microtiter plate. After a further incubation period of 1 hour at 20° C., by washing with TBS buffer (50 mmol/l tris-(hydroxymethyl)-aminomethane, 1 mmol/l $MgCl_2$, 50 mmol/l NaCl, pH 7.8 with HCl, 0.05% of polyoxyethylene sorbitan monooleate) all the molecules which are not bonded on the antibody positions are removed. For the quantitative detection of the bonded enzyme tracer, respectively 125 $\mu l$ phosphatase substrate solution (1 mg p-nitrophenylphosphate per ml carbonate buffer) are poured into the individual cavities. The enzyme reaction takes place at 20° C., but can be accelerated by incubation at higher temperature. The absorption of the solution in the individual cavities is measured by a vertical ray photometer on the wavelength 4054 nm. If it is wished to move into the range of higher sensitivities, overnight incubation at 4° C. is recommended. But it must be recalled that without special demands on reagent, device and spatial unit reproducible results in the ppt range are not attainable. The computation of the antigen concentration of the sample is based on the following background. The enzyme tracer bonds at first with the free antibody bonding positions, which are left over after incubation with the sample antigen. Thus in the presence of high concentrations of sample antigen only few enzyme tracers are bonded, but with lower concentration of sample antigens, on the other hand, many enzyme tracers are bonded. The amount of the bonded enzyme tracer is therefore a function of the sample antigen concentration. The absorption of the reacted substrate amount (color reaction from colorless to yellow) is used as the measurement magnitude for the bonding of the enzyme tracer.

Computation

Absorption ratio of unknown sample ($B = A_B A_{uB}$) and zero sample ($BO = A_{BO} - A_{uB}$):

$$B/BO = (A_B - A_{uB1})/(A_{BO} - A_{uB})$$

(B/BO): ratio of the enzyme tracer binding in the presence of an antigen(B) in relation to the enzyme tracer binding in the absence of an antigen (BO).

$A_{BO}$: absorption (405 nm) as measure for the enzyme tracer binding in the absence of antigen (herbicide).

$A_B$: absorption (405 nm) as measure for the enzyme tracer binding in the presence of an unknown concentration of antigen(herbicide) in sample.

$A_{UB}$: absorption (405 nm) as measure for the enzyme tracer binding in the absence of antibodies covering the walls of the cavities.

If B/BO is entered on the y axis against the logarithm of the herbicide concentration, a sigmoid curve results. For linearization for better handling it is proposed that the y axis should also be logarithmed (logit/log transformation). For evaluation it has been found to be better to transform the degree of inhibition (1−B/BO) over the integral of the normal distribution. In practice one enters the percentage inhibition (100* (1−B/BO) instead of frequency in the probability paper. Thereby the sigmoid curve is linearized.

The detection process for the sample antigen can be carried out so that in the individual test series, the sample antigen is reacted with each of the antibodies employed separately or consecutively. In the latter method a result is that during each test series the same inhibition is observed during detection if the exposed portions towards which the various antibodies are preferably oriented are present in different molecules. However, if at least two exposed sides are included in a molecule, there are deviations. This is explained by the fact that a molecule which possesses two of the initially named exposed sides is removed by the antibody binding on one side as well as on the other from the solution and after the transfer of the solution to the next cavity, it is no longer available for binding. If this is carried out for all the binding possibilities, the following inhibition matrix (table 2) results, from which the basic structures can be derived in a multi-process.

TABLE 2

| 1. test series: | | | 2. test series | | | 3. test series: | | | Inhibition matrix |
|---|---|---|---|---|---|---|---|---|---|
| A | B | C | B | C | A | C | A | B | |
| + | + | + | + | + | + | + | + | + | all sides (II), (III), (IV) are present independently (3 components) |
| + | − | − | + | − | − | + | − | − | all sides (II), (III), (IV) are in |

TABLE 2-continued

| 1. test series: | | | 2. test series | | | 3. test series: | | | Inhibition matrix |
|---|---|---|---|---|---|---|---|---|---|
| A | B | C | B | C | A | C | A | B | |
| | | | | | | | | | one molecule (one component) |
| + | − | + | + | + | − | + | + | − | sides (II) and (III) are present in one molecule (two components) |
| + | + | − | + | + | − | + | − | + | sides (II) and (IV) are present in one molecule (two components) |
| + | + | − | + | − | + | + | + | − | sides (III) and (IV) are present in one molecule (two components) |

+ = inhibition of the enzyme tracer binding
− = no inhibition of the enzyme tracer binding
The inhibition matrix shown here can easily be expanded beyond C by the use of other antibodies, in order to analyze still more complicated molecules or molecule mixtures

EXAMPLE 2

The cross-reactivity of triazines was investigated with representatives of the substance classes which are listed in table 3, in order to be above to classify these compounds with respect to their activity classes. The immunization is carried out in such a way that specifically the alkyl-, isopropyl- and ethyl radicals were exposed in order to obtain a high specificity for atrazine. In the following table the inhibition values (%) of the important representatives of individual substance classes are listed. A strong bonding of an antigen on an antibody causes an equally strong inhibition of the enzymatic detection system. From the strength of the inhibition, the degree of interaction between the antibody and the antigen can be recognized.

TABLE 3

| Cross-activity of various herbicides at a concentration of 2 ppb | | |
|---|---|---|
| Substance class: | compound: | inhibition (%): |
| triazines | atrazine | 6.0 |
| | hydroxy-3 isopropyl-5-ethyltriazine | 5.3 |
| | ametryn | 21.4 |
| | desethylametryn | 16.8 |
| | desisopropylametryn | 16.5 |
| anilides | metazachlor | 15.2 |
| ureas | metabenzthiazuron | 8.3 |
| trifluorobenzimidazole | fenazaflor | 4.4 |
| aminotriazines | metribuzine | 6.7 |
| uracile | bromazile | 11.1 |

The inhibition values shown in table 3 indicate that in the given concentration range (2 ppb) the selectivity of the antibodies is not so strongly marked, but that the listed compounds which also take effect on the photosystem II can equally be distinguished in an immunological detection process.

Using the inventive concept of the immuno-assay, it is possible by the calculated use of cross-reactivities to draw conclusions concerning the structure of the substances individually present in a mixture (compare example 1).

The foregoing disclosure and description of the invention are illustrative and explanatory thereof, and various changes in the size, shape and materials, as well as in the details of the illustrated invention may be made without departing from the spirit of the invention.

We claim:

1. A competitive immunological process for the determination of the presence of herbicides comprising:
forming an antigen-coupled carrier matrix by coupling a compound of the formula:

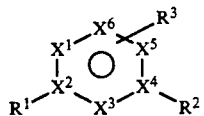

where:

$X^1, X^3, X^5$ are carbon or nitrogen;
$X^2, X^4, X^6$ are carbon;
$R^1$ is the group HN $(C_nH_{2n+1})$ wherein n is the integer from 0 to 8;
$N(C_mH_{2m+1})_2$, where m is the integer 1 to 8;
$HN-C_nH_{2n}Y$, where Y is a cyano-, amino- or a group and n is the integer 1 to 8;
$C_xH_{2x}Z$, where Z is a cyano-, amino, or COOH group, and s is the integer 1 to 8;
azide, halogen, an SH group, an OH group or a HN-$C_6H_4Cl$ group;
$R^2$ is a group $HNC_qH_{2q+1}$, where q is an integer from 0 to 8; $N(C_rH_{2r+1})$ where r is the integer 1 to 8;
$HN-C_qH_{2q}Y$ where Y is a cyano-, amino, azido- or a COOH group and q is the integer 1 to 8;
$N(C_4H_{2r+1})Z$, where Z is cyano-, amino-, azido-, or COOH group or is a $C_qH_{2q}$ group, and r is a integer from 1 to 8 an q is an integer from 1 to 8;
azide, halogen, an SH group or an OH group;
$R^3$ is halogen; $SC_nH_{2n+1}$ where n is an integer from 0 to 8; $OC_nH_{2n+1}$ where n is an integer from 0 to 8; a cyano-, amino-, carboxyl-, or a CHO group, where the substituent R3 is either in the meta position to R1 and R2 or may be in ortho- or para-position to $R^1$ and $R^2$, to a carrier matrix via a substituent selected from the group comprising said $R_1, R_2$, and $R_3$ to expose only a portion of said compound;
immunizing laboratory animals with said antigen-coupled carrier matrix to obtain antibodies which respond to said exposed portion of said compound;
extracting said antibodies;
reacting a test sample with at least two of said antibodies in a test series simultaneously or sequentially and with at least two labeled antigens which compete with said sample to bind to said antibodies, wherein each of said antibodies are obtained from immunization with antigen-coupled carrier matrices which are coupled through different said substituents $R_1, R_2, R_3$ and thus respond to different said exposed portions of compound and wherein each of said labeled antigens correspond to said exposed portion of said compound used to raise said antibody; and
determining the qualitative and quantitative presence of said compound in said sample based on the amount of labeled antigens bound to said antibodies.

2. The process of claim 1, wherein said compound is a meta-substituted, aromatic, six-membered ring which contains up to 3 nitrogen atoms.

3. The process of claim 2 wherein said compound is selected from the group consisting of pyridine, pyrimidine, and triazine.

4. The process of claim 1, wherein three antibodies designated A, B, and C raised against three different exposed portions of said compound by forming three antigen-coupled carrier matrices coupled respectively via said substituents $R^1, R^2$, and $R^3$ are used in a test series having the following sequence:

test series: A B C;
test series: B C A; or
test series: C A B.

5. The process of claim 2, wherein three antibodies designated A, B, and C raised against three different exposed portions of said compound by forming three antigen-coupled carrier matrices coupled respectively via said substituents $R^1, R^2$, and $R^3$ are used in a test series having the following sequence:

test series: A B C;
test series: B C A; or
test series: C B A.

6. The process of claim 1, wherein said sample is reacted separately and sequentially with each of said antibodies.

7. The process of claim 4, wherein said sample is reacted separately and sequentially with each of said antibodies.

8. The process of claim 1, wherein said sample is first reacted with one antibody of said at least two antibodies, the non-reacted supernatant is separated, and said supernatant is subsequently reacted with the second of said at least two antibodies.

9. The process of claim 4, wherein said sample is first reacted with one antibody or said three antibodies, the non-reacted supernatant is separated, said supernatant is subsequently reacted with the second of said three antibodies, the non-reacted supernatant is separated, and said supernatant is subsequently reacted with the third of said three antibodies.

10. The process of claim 1, wherein said antibodies are monoclonal antibodies.

11. The process of claim 1, wherein said label of said labeled antigen is selected from the group consisting of radioactive isotope, enzyme, fluorescent substance and substance which emits an electrical signal.

12. The process of claim 4, wherein said label of said labeled antigen is selected from the group consisting of radioactive isotope, enzyme, fluorescent substance and substance which emits an electrical signal.

* * * * *